United States Patent [19]

Goe et al.

[11] Patent Number: 5,099,028
[45] Date of Patent: Mar. 24, 1992

[54] PROCESS FOR THE SYNTHESIS OF 4-AMINO-1,2,4-(4H)TRIAZOLE DERIVATIVES

[75] Inventors: Gerald L. Goe; Eric F. V. Scriven, both of Greenwood; James G. Keay, Indianapolis; Lowell M. Huckstep, Plainfield, all of Ind.

[73] Assignee: Reilly Tar and Chemical Corporation, Indianapolis, Ind.

[21] Appl. No.: 455,821

[22] Filed: Dec. 19, 1989

Related U.S. Application Data

[63] Continuation of Ser. No. 262,198, Oct. 19, 1988, abandoned, which is a continuation of Ser. No. 933,786, Nov. 24, 1986, abandoned.

[51] Int. Cl.⁵ ............................................. C07D 249/14
[52] U.S. Cl. ................................................... 548/265.6
[58] Field of Search ....................................... 548/265.6

[56] References Cited

FOREIGN PATENT DOCUMENTS

| 216554 | 9/1984 | Czechoslovakia | 548/266 |
| 2822014 | 11/1978 | Fed. Rep. of Germany. | |
| 7135056 | 7/1969 | Japan | 548/266 |
| 0028174 | 3/1978 | Japan | 548/266 |
| 1203091 | 1/1985 | U.S.S.R. | 548/266 |

OTHER PUBLICATIONS

Valcke et al., Proc.-Annu. Meet. Am. Wood-Preserv. Assoc. 1985, 81, 196.
Jager, Pestic. Chem. Hum. Welfare Environ., Proc. Int. Congr. Pestic Chem., 5th, vol. 1, pp. 55-65.
Kucharski and Chodan, Zasz. Nauk, Akad. Roln-Tech. Olsztynie, Roln., 36, 109–116 (Chem. Abstr., 101, 129600 (1984)).
Organic Syntheses (vol. 24, p. 12, 1944).
Herbst and Garrison (J. Org. Chem., 18, 872 (1953)).
Mizushima et al., (Japan Pat. No. 71 35,056 (1971), Chem. Abstr., 76, 3867 (1972).
Jaromir and Jaromir (Czech. Patent 216,554, (1984), Chem. Abst. 103, 160520 (1985).
Krieble et al., "Amide Hydrolysis with etc." *JACS* (1938) 60 2976.
J. March, *Advanced Organic Chemistry*, 3rd Ed., Wiley-Interscience, 1985, p. 338.
B. C. Challis et al., *The Chemistry of Amides*, Ed. J. Zabicky, Interscience, 1970, p. 816.
Krysin et al., "Amino derivatives of 1,2,4-triazole," CA 84:90156s 1976.
Socha et al. II, "4-Amino-4H-1,2,4-triazole," CA 101:191930q 1984.
Socha et al. III, "4-Amino-4H-1,2,4-triazole," CA 105:208889r.

Primary Examiner—Patricia L. Morris
Attorney, Agent, or Firm—Woodard, Emhardt, Naughton, Moriarty & McNett

[57] ABSTRACT

A process for preparing a 4-amino-1,2,4-(4H)triazole derivative compositions having the formula

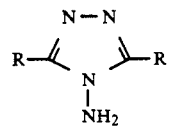

wherein R is hydrogen or an alkyl group containing from 1 to about 10 carbon atoms, which alkyl group can be additionally substituted by one or more aryl, heteroaryl, hydroxy, or alkenyl substituents, comprising the step of reacting hydrazine or an aqueous hydrazine solution with a carboxylic acid having the formula RCO$_2$H in the presence of an insoluble polymer containing acidic functional groups sufficiently strong to cause the reaction to proceed under mild conditions to produce a product of high yield and purity.

19 Claims, No Drawings

PROCESS FOR THE SYNTHESIS OF 4-AMINO-1,2,4-(4H)TRIAZOLE DERIVATIVES

This application is a continuation of application Ser. No. 262,198, filed Oct. 19, 1988 now abandoned which is a continuation of application Ser. No. 933,786, filed Nov. 24, 1986 now abandoned.

BACKGROUND OF THE INVENTION

This invention relates generally to the field of heterocyclic chemistry and the synthesis of nitrogen heterocycles, and more specifically to a novel process for the synthesis of derivatives of 4-amino-1,2,4-(4H)triazole from hydrazine and carboxylic acids.

Derivatives of 4-amino-1,2,4-(4H)triazole have well-known utility as intermediates in the synthesis of a large number of 1,2,4-triazole compounds that are utilized as herbicides (e.g., German Patent Nos. 2,653,447 and 2,822,014), plant growth regulators (e.g., German Patent No. 2,737,489 and British Patent No. 2,050,334), and as fungicides (e.g., Chem. Abstr., 104, 124849 (1986); Valcke et al. Proc.-Annu. Meet. Am. Wood-Preserv. Assoc. 1985, 81, 196. also Jager, Pestic. Chem. Hum. Welfare Environ., Proc. Int. Congr. Pestic. Chem., 5th, Vol. 1, pp. 55–65). In addition, 4-amino-1,2,4-(4H)triazole itself has well-known utility as a nitrification inhibitor (e.g., U.S. Pat. No. 3,697,244; Kucharski and Chodan, Zasz. Nauk, Akad. Roln-Tech. Olsztynie, Roln., 36, 109–116 (Chem. Abstr., 101, 129600 (1984)).

The synthesis of 1,2,4-triazole derivatives has been well-explored, and is generally reviewed in C. Temple, Jr., "Triazoles 1,2,4," *The Chemistry of Heterocyclic Compounds*, Vol. 37, John Wiley & Sons, Inc., New York, 1981. One process for the synthesis of 4-amino-1,2,4-(4H)triazole is described in Organic Syntheses (Vol. 24, p. 12, 1944) in which ethyl formate and 85% hydrazine hydrate are combined, then heated at progressively higher temperatures, first distilling ethanol and then water out of the reaction mixture, and then heating the remaining residue up to 200° C. the residue, while still hot, is treated with solvents, and after extensive manipulation crystallized 4-amino-1,2,4-(4H)triazole is reportedly obtained in a 65%–71% yield. This process is undesirable because it requires the use of flammable and volatile ethyl formate, it requires close temperature control and high temperatures, and it reportedly produces the product in only moderate yield. Furthermore, the 4-amino-1,2,4-(4H)triazole is of low purity, requiring the use of decolorizing carbon. The recovered wet ethanol by-produce is of little or no value unless further costly procedures are used to purify it.

Herbst and Garrison (J. Org. Chem., 18, 872 (1953)) disclosed the preparation of a series of 3,5-dialkyl-1,2,4-(4H)triazoles by an uncatalyzed process requiring the heating of hydrazine hydrate with carboxylic acids while removing water by distillation. The process requires excessively high temperatures of 200° to 280° C., and the yields of some substituted products utilizing this process are unacceptably low and poorly reproducible.

Mizushima et al. (Japan Patent No. 71 35,056 (1971); Chem. Abstr., 76, 3867 (1972)) disclosed the reaction of formic acid with hydrazine hydrate and phosphoric acid at 160°–180° C. to give 96.6% yield of 4-amino-1,2,4-(4H)triazole. However, the product of this process if also of extremely low purity because phosphoric acid remains in the product, rendering it unsuitably inpure for most uses.

More recently, Jaromir and Jaromir [Czech. Patent 216,554, (1984); Chem. Abst., 103, 160520 (1985)] disclosed the reaction of formamide and hydrazine in the presence of a strongly acid ion exchange resin catalyst, first using heat and vacuum to remove ammonia and water produced during the reaction, and then heating to 220° C., preferably to 160°–180° C., which are uncomfortably high temperatures, for a period of time to complete the reaction. The ion exchange resin is reportedly removed from crude product at an elevated temperature of 100° C., and 4-amino-1,2,4-(4H)triazole is crystallized from the melt in 80%–85% yield, leaving unreacted formamide that must be recovered and recycled. This process also suffers from the disadvantages of producing a by-product of unsubstituted 1,2,4-triazole, which results in an impurity in the desired 4-amino-1,2,4-(4H)triazole, as well as a lower yield of 4-amino-1,2,4-(4H)triazole.

Applicants' discovery overcomes these inadequacies in the existing art, and results in the synthesis reaction proceeding at attractively lower temperatures much more suitable for commercial manufacturing operations, with no significant by-products, resulting both in easier product separation and in high yields and purity particularly in the case of 4-amino-1,2,4-(4H)triazole.

SUMMARY OF THE PRESENT INVENTION

As one embodiment of the Applicants' invention there is provided a process for preparing a 4-amino-1,2,4-(4H)triazole derivative composition having the formula

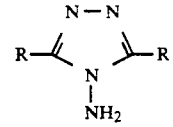

wherein R is hydrogen or an alkyl group containing from 1 to about 10 carbon atoms, which alkyl group can additionally be substituted by one or more aryl, heteroaryl, hydroxy, or alkenyl substituents. This process comprises the step of reacting hydrazine or an aqueous hydrazine solution with a carboxylic acid having the formula $RCO_2H$ in the presence of an acidic ion exchange resin which comprises an insoluble polymer containing acidic functional groups sufficiently strong to cause the reacting step to proceed. In their preferred forms, these synthesis reactions proceed under mild conditions at temperatures of about 150°–180° C. and produce high yields and purity, particularly in the most preferred embodiment where R is hydrogen, thereby evidencing substantial advantages over what have been reported in the past. Moreover, the 4-amino-1,2,4-(4H)triazole derivatives produced thus far utilizing Applicants' preferred processes have exhibited excellent crystal structures, were easily filtered, and have been shown to be less hygroscopic than when produced by other reported methods.

Related objects and advantages of the present invention will be apparent from the following description.

DESCRIPTION OF THE PREFERRED EMBODIMENT

As stated previously, one embodiment of Applicants' invention comprises a novel process for the synthesis of 4-amino-1,2,4-(4H)triazole derivative compositions having the formula

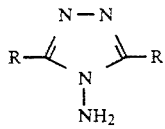

wherein R is hydrogen or an alkyl group containing from 1 to about 10 carbon atoms, which alkyl group can be additionally substituted by one or more aryl, heteroaryl, hydroxy, or alkenyl substituents. The preferred process comprises the step of reacting hydrazine or an aqueous hydrazine solution with a carboxylic acid having the formula $RCO_2H$, where R is as defined above, in the presence of a particular acidic ion exchange resin catalyst. The preferred catalyst within the scope of Applicants' invention is an insoluble polymer containing acidic functional groups sufficiently strong to cause the reacting step to proceed. In this regard, the relative strength required in such an acid to catalyze the reaction is a matter common to the art, either being already known or reported in the literature for various acid candidates or at least a matter well within the ordinary skill of a person in the art to determine. Examples of preferred functional groups known by Applicants to have such requisite strength include sulfonic acids and phosphonic acids, although this listing is in no way limiting of the scope or breadth of Applicants' invention as disclosed and claimed herein.

Similarly, examples of typical commercially available acidic ion exchange resins which are useful with Applicants' preferred embodiments are the following: sulfonated cross-linked polystyrene, such as those which have been marketed under the trademarks Amberlyst A-15 and Amberlite 200 by Rohm & Haas; perfluorinated sulfonic acids, such as Nafion marketed by DuPont; and phosphonic acids, such as Duolite ES-63 marketed by Diamond Shamrock, Bio-Res 63 marketed by Bio-Rad, and Nalco X-219 marketed by Nalco. Aside from these specific resins, others within the definition above, whether now available or yet to be synthesized, would also work in Applicants' preferred process and for that reason are considered within the scope of the invention as disclosed and claimed herein.

In their work to data, Applicants have surprisingly discovered that the catalyzed reactions which occur utilizing their preferred process take place at significantly lower temperatures than what is required for such reactions in the absence of Applicants' catalysts. This is particularly important because the high temperatures used in the absence of a catalyst (200°-280° C.) are dangerously high and close to the maximum operating temperatures of the majority of glass-lined chemical process equipment on the market. The catalyzed reactions of Applicants' preferred processes are also carried on over shorter time periods than in the absence of a catalyst, leading to potential higher productivity of a given chemical plant.

One possible theory as to the chemistry of Applicants' preferred process is that when the two reactants of the process are mixed in the presence of the Applicants' disclosed catalysts, two intermediates are formed, the first being

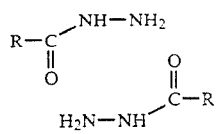

and the second being

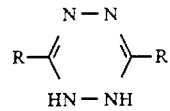

The latter of these intermediates, in the presence of the Applicants' preferred catalyst, is then catalyzed to the desired product shown by the following formula when simply heated to moderate temperatures up to about 150° C., as further defined herein.

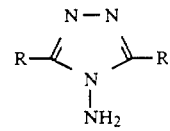

In the absence of the Applicants' catalyst invention, one possible explanation is that this final step may be able to be catalyzed to some extend by the use of certain acid salts or the acids themselves as shown in the art, but only where the reaction temperature is raised appreciably to about 200° C. or higher or where the reaction is allowed to run for an extended period of time. In the preferred case where R is hydrogen, however, such elevated temperatures and reaction periods are unacceptable because they approach the decomposition point of the material itself.

Applicants have also surprisingly discovered that the recovered yields, particularly of 4-amino-1,2,4-(4H)triazole itself, utilizing their preferred process are of extremely high and consistent purity. Commercially significant yields have also been produced of derivative compositions from testing performed to date, although no effort has as yet been made to maximize yield or purity in these cases. Applicants have encountered no acid salts such as would need to be removed from the crude prior art products. Because of their purity, Applicants' products have exhibited excellent crystal structures and are easily filtered, and have been shown to be less hygroscopic than when produced by other methods.

Other advantages of Applicants' preferred process are many. For example, the preferred solid ion exchange resin catalyst is very easy and safe to handle as compared to the mineral acids used in the prior art. Furthermore, the resin can be easily removed from the product solution by simple filtration or similar methods, and can be recycled many times without regeneration. Because the process of Applicants' invention gives extremely high yields and extremely small quantities of unwanted by-products, the filtrate is also easily recyclable thus conserving reactants and solvents. The products themselves are typically a white crystalline substance having excellent appearance and are easy and safe to recover because filtration of a molten solid is not necessary as in some prior art processes. Applicants' reactions using formic acid give water as a by-product, while other reported procedures yield alcohol or ammonia which are difficult to recycle or dispose or properly.

Examining more closely the preferred reacting step of Applicants' process, it includes combining of the desired carboxylic acid with a slight stoichiometric excess of hydrazine or an aqueous hydrazine solution in the presence of an insoluble polymer containing acidic functional groups sufficiently strong to cause the reacting step to proceed, and then causing the resultant mixture to be at a temperature sufficiently high and for such length of time as to cause substantial reaction to occur. The importance of the preferred polymer is that it be effectively insoluble, whether through cross-linking as in many copolymer arrangements or through sheer molecular size, or the like, and that it adequately support the acidic functional groups already discussed. Examples of suitable polymers have been given above, but this listing is only exemplary and not limiting of the scope of Applicants' invention. The physical structure of such insoluble polymers are also varied, with porous beads or powders or some other layered or similar structure being preferred at this time for reasons of ease of separation and recovery for subsequent reuse.

No specific temperature, time period, or other reaction conditions or equipment are required from Applicants' work to date. As to temperature, experiments have indicated that a lower temperature range of about 105°-180° C. As to length of reaction, for being about 110°-150° C. As to length of reaction, for commercial application of Applicants' preferred process, experiments to data have not shown this causing step needs to be maintained for any critical period of time. In the preparation of 4-amino-1,2,4-(4H)triazole, for example, maintaining the reaction a sufficient time to provide a yield of at least about 80% is preferred. However, other specific desired or required yields understandably vary with the particular commercial need and product involved. Testing to data has shown that yields of at least about 80% of the 4-amino-products have been achieved with periods of about 6 hours, although many factors affect this result. Moreover, such results have been achieved at atmospheric pressures which is a significant improvement over prior art processes requiring elevated pressures often accompanying elevated temperatures as well. Testing has further shown that use of a solvent at the end of a reaction is beneficial in assisting rapid separation and recovery of the catalyst for later reuse.

For the purpose of further promoting a better understanding of the preferred process of Applicants' invention, reference will now be made in the examples below to the preparation of specific 4-amino-4H-1,2,4-triazole derivatives within the defined classification. No limitation of the scope of the breadth of Applicants' invention is thereby intended.

EXAMPLE 1

4-amino-1,2,4-(4H)triazole

91% Formic acid (471.0 g, 9.29 mole) was added to a mixture of 100% hydrazine hydrate (474.4 g. 9.48 mole) and Amberlyst 15 resin (46 g) at a rate such that the exothermic reaction could be controlled. The reaction temperature after mixing was 110° C. Heat was applied and the water was distilled from the reaction mixture until the reaction temperature reached 150° C. The reaction temperature was held at 150° C. for 6 hours collecting any distillate that came over. At the conclusion of the reaction period, the reaction mixture was cooled to 80° C. and isopropanol (500 ml) was added maintaining the temperature at 75°-80° C. The resin was then removed by simple filtration and washed with additional isopropanol (150 ml). The combined isopropanol filtrates were allowed to cool to precipitate the 4-amino-1,2,4(4H)-triazole. The product was filtered and washed with some cold isopropanol. The filtrates were concentrated to give a second crop of 4-amino-1,2,4-(4H)triazole that was also filtered and washed with some cold isopropanol. The entire wet cake was dried to give an 85% yield of 4-amino-1,2,4-(4H)triazole of 99.5% purity, m.p 87°-89° C. This product, as well as those of the examples which follow, have demonstrated and known utility in several areas such as the specific uses mentioned in the Background section of this application.

EXAMPLE 2

4-amino-1,2,4-(4H)triazole: Resin Recycle

91% Formic acid (357.3 g, 7.05 mole) was added to a mixture of 100% hydrazine hydrate (359.9g, 7.19 mole) and Amberlyst 15 resin (42 g) at a controlled rate. The reaction temperature was 105° C. at the end of the addition. The reaction mixture was heated and the water removed by distillation to a reaction temperature of 150° C. The reaction mixture was then held at 150° C. for 6 hours. At the end of 6 hours, the reaction mixture was cooled to 80° C. and isopropanol (400 ml) was added to dissolve the product. The isopropanol solution was kept at 75°-80° C. and was drained from the flask leaving the resin in the flask. Another portion of isopropanol (200 ml) was added to the flask to wash the resin and was drained from the flask. At this point, the flask was re-charged with an equivalent amount of 100% hydrazine hydrate and another charge of 91% formic acid was added to it in the same manner for the next run. The isopropanol solution was cooled to precipitate the product. The product was filtered and washed with cold isopropanol. The isopropanol filtrate was saved for recycle in the next run. At the conclusion of the second run, performed as the first, the reaction mixture was again cooled to 80° C. and isopropanol filtrate (400 ml) from the first run was added to dissolve the product. The isopropanol solution was drained from the flask and more isopropanol filtrate (200 ml) was added to the flask to wash the resin. This filtrate was drained and the flask was re-charged and a third run performed. The isopropanol solution was again cooled to precipitate the product. The product was filtered and washed with some cold isopropanol. The isopropanol filtrate was used in the third run. The third run was performed and worked up as the two previous runs. After the product had crystallized and was filtered and washed, the entire isopropanol filtrate was concentrated to give a second crop of product that was filtered and washed with cold isopropanol. The wet filter cakes were combined and dried to give an overall 91% yield of 4-amino-1,2,4-(4H)triazole, for the three runs, of 99.4% purity, m.p. 87°-89° C.

EXAMPLE 3

3,5-Dimethyl-4-amino-1,2,4(4H)triazole

Glacial acetic acid (242.8 g, 4.04 mole) was added to 85% hydrazine hydrate (243.0 g, 4.12 mole) and Amberlyst 15 resin (20 g) at a rate such that the reaction temperature did not exceed 115° C. Heat was then applied and the water was removed by distillation to a reaction temperature of 180° C. The reaction mixture was then held at 180° C. for 6 hours. The reaction mixture was then cooled to 80° C. and dissolved in methanol (500 ml). The resin was removed by simple filtration and washed with some methanol. The methanol filtrate was cooled to precipitate the product. The product was filtered and washed with some cold methanol. The combined filtrates were concentrated to give a second crop of product which was filtered and washed with cold methanol. The wet filter cakes were dried to give an 80% yield of 3,5-dimethyl-4-amino-1,3,4(4H)triazole of 99.2% purity, m.p. 201°-203° C.

EXAMPLE 4

3,5-Diethyl-4-amino-1,2,4-(4H)triazole 3,5-Diethyl-4-amino-1,2,4-(4H)amino-1,2,4-(4H)triazole was effectively made by the procedure described in Example 3 using propionic acid in place of formic acid.

EXAMPLE 5

3,4,-Di-n-propyl-4-amino-1,2,4(4H)triazole 3,4-Di-n-propyl-4-amino-1,2,4-(4H)triazole was effectively made by the procedure described in Example 3, except the reaction temperature was raised to 200° C., using butyric acid in place of formic acid.

EXAMPLE 6

3,5-Diisopropyl-4-amino-1,2,4-(4H)triazole 3,5-Diisopropyl-4-amino-1,2,4-(4H)triazole was effectively made by the procedure described in Example 3, except the reaction temperature was raised to 210° C., using isobutyric acid in place of formic acid.

EXAMPLE 7

3,5-Di(hydroxymethyl)-4-amino-1,2,4-(4H)triazole 3,5-Di(hydroxymethyl)-4-amino-1,2,4-(4H)triazole was effectively made by the procedure described in Example 1 using glycolic acid in place of formic acid.

EXAMPLE 8

The process of Example 1 was carried out except that an equivalent amount of hydrazine in the form of 85% hydrazine hydrate was used. Comparable results were obtained.

EXAMPLE 9

3,5-Di(3-Butenyl)-4-Amino-1,2,4(4H)triazole 3,5-Di(3-Butenyl)-4-Amino-1,2,4(4H)triazole was effectively made by the procedure described in Example 1 using 4-pentenoic acid in place of formic acid.

EXAMPLE 10

3,5-Dibenzyl-4-Amino-1,2,4-(4H)Triazole 3,5-dibenzyl-4-amino-1,2,4-(4H)triazole was made by the procedure described in Example 3 using phenylacetic acid in place of formic acid.

EXAMPLE 11

3,5-Diphenethyl-4-Amino-1,2,4-(4H)Triazole 3,5-diphenethyl-4-amino-1,2,4-(4H)triazole was made by the procedure described in Example 3 using 3-phenylpropanoic acid in place of formic acid.

EXAMPLE 12

3,5-Dinonyl-4-Amino-1,2,4-(4H)Triazole 3,5-dinonyl-4-amino-1,2,4-(4H)triazole was made by the procedure described in Example 3 using decanoic acid in place of formic acid.

What is claimed is:

1. In a process for preparing a 4-amino-1,2,4-4(H)triazole derivative composition having the formula

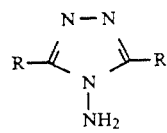

wherein:
R is hydrogen or an alkyl group containing from 1 to 10 carbon atoms, which alkyl group can be additionally substituted by one or more aryl, heteroaryl, hydroxy, or alkenyl substituents, which includes the step of reacting hydrazine or an aqueous hydrazine solution with a carboxylic acid having the formula $RCO_2H$, the improvement which comprises conducting said reaction in the presence of an insoluble polymer containing acidic functional groups sufficiently strong to and which cause the reacting step to proceed.

2. The process of claim 1 in which R is hydrogen.

3. The process of claim 1 in which R is methyl.

4. The process of claim 1 in which the acidic functional groups are sulfonic acids.

5. The process of claim 4 in which the insoluble polymer in said reacting step is sulfonated cross-linked polystyrene.

6. The process of claim 1 in which the acidic functional groups are phosphonic acids.

7. The process of claim 1 in which the acidic functional groups are perfluorinated sulfonic acids.

8. The process of claim 1 comprising the additional step of recovering polymer after said reacting through filtration means and without the need for regeneration before subsequent reuse.

9. The process of claim 4, 5 or 8 in which R is hydrogen.

10. The process of claim 1 in which said reacting is carried out at a temperature that ranges from about 105° to about 180° C.

11. The process of claim 1 in which said reacting is carried out at a temperature that ranges from about 110° to about 150° C.

12. The process of claim 1 in which said reacting includes the step of combining the reactants in a vessel and causing the resultant mixture to be at a temperature sufficiently high and for such a length of time as to provide a yield of the desired product at least about 80%.

13. The process of claim 1 or 12 in which said reacting is sufficient to provide the desired product at about 99% purity.

14. The process of claim 13 comprising the additional steps of isolating and recovering the desired product after said reacting.

15. The process of claim 9 in which water is distilled out of the reaction mixture during said reacting.

16. The process of claim 14 in which said reacting is carried out in a continuous manner.

17. The process of claim 14 comprising the additional step of recovering polymer after said reacting through filtration means and without the need for regeneration before subsequent reuse.

18. The process of claim 17 comprising the additional step of using a solvent to acid in said recovering of the insoluble polymer after said reacting.

19. The process of claim 1 in which said reacting is at atmospheric pressure.

* * * * *

UNITED STATES PATENT AND TRADEMARK OFFICE
CERTIFICATE OF CORRECTION

PATENT NO. : 5,099,028

DATED : March 24, 1992

INVENTOR(S) : Gerald L. Goe, et al

It is certified that error appears in the above-identified patent and that said Letters Patent is hereby corrected as shown below:

In column 1, line 42, please change "200° C. the residue" to --200° C. The residue--.

In column 1, line 68, please change "if" to --is--.

In column 3, line 45, please change "Bio-Res" to --bio-Rex--.

In column 4, line 33, please change "extend" to --extent--.

Col. 5, lines 32-33, delete, "As to length of reaction, for being about 110°-150°C." and insert --is preferred, with the most preferred range being about 110°-150°C--.

In column 5, line 35, please change "data" to --date--.

Signed and Sealed this

Thirteenth Day of July, 1993

Attest:

MICHAEL K. KIRK

*Attesting Officer*     *Acting Commissioner of Patents and Trademarks*